United States Patent [19]

Aranyi

[11] Patent Number: 5,193,731
[45] Date of Patent: Mar. 16, 1993

[54] ANASTOMOSIS SURGICAL STAPLING INSTRUMENT

[75] Inventor: Ernest Aranyi, Easton, Conn.

[73] Assignee: United States Surgical Corporation, Norwalk, Conn.

[21] Appl. No.: 584,206

[22] Filed: Sep. 18, 1990

Related U.S. Application Data

[62] Division of Ser. No. 214,289, Jul. 1, 1988, Pat. No. 5,005,749.

[51] Int. Cl.⁵ ............................................. A61B 17/115
[52] U.S. Cl. ..................................... 227/19; 227/179
[58] Field of Search .................. 173/20; 227/182, 121, 227/19, 175, 178, 179, 180, 8; 116/225, 230, 279, 281, 325

[56] References Cited

U.S. PATENT DOCUMENTS

| | | | |
|---|---|---|---|
| 3,480,087 | 11/1969 | Boeger | 173/20 |
| 4,351,466 | 9/1982 | Noiles . | |
| 4,379,457 | 4/1983 | Gravener et al. . | |
| 4,406,392 | 9/1983 | Campbell et al. . | |
| 4,527,724 | 7/1985 | Chow et al. . | |
| 4,540,110 | 9/1985 | Bent et al. | 227/19 |
| 4,576,167 | 3/1986 | Noiles | 227/19 |
| 4,603,693 | 8/1986 | Conta et al. . | |
| 4,606,343 | 8/1986 | Conta et al. . | |
| 4,646,745 | 3/1987 | Noiles . | |
| 4,930,503 | 6/1990 | Pruitt . | |

Primary Examiner—Frank T. Yost
Assistant Examiner—Allan M. Schrock
Attorney, Agent, or Firm—Thomas R. Bremer

[57] ABSTRACT

The anastomosis surgical stapling instrument is provided with a slide plate within the yoke which is responsive to the movement of the center rod in order to block the movement of safety lock prior to positioning of the anvil assembly in a position for firing of the staples. The slide plate is bias by a spring to follow the movement of the center rod. Further, the center rod is provided with a recessed portion to provide a clearance for the arms of the handles so that jamming of the center rod is avoided after firing of the staples. An indicator is also provided to positively indicate when the staples have been fired. This indicator is mounted in the side of the yoke and is responsive to the movement of the pusher tube.

9 Claims, 8 Drawing Sheets

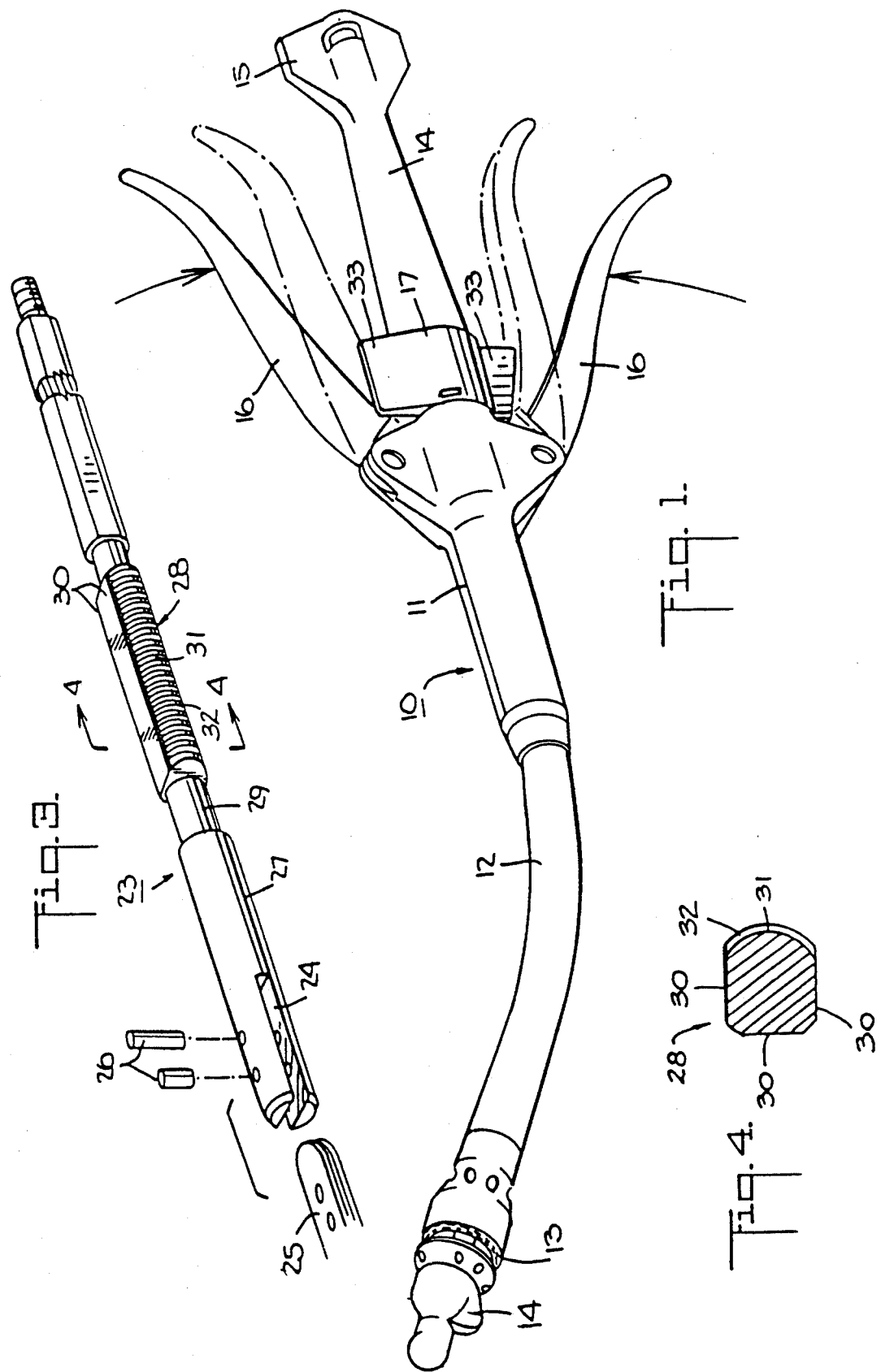

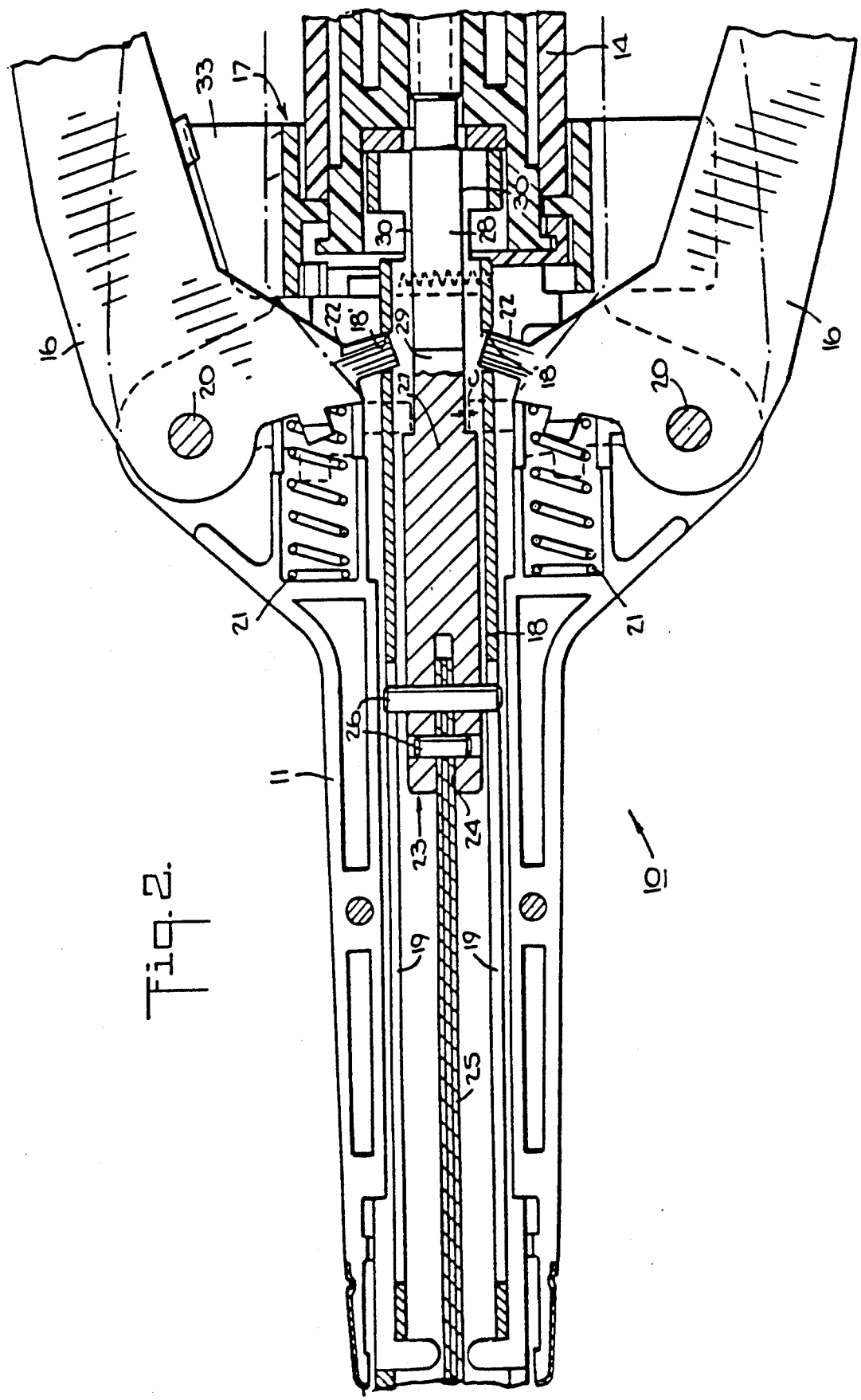

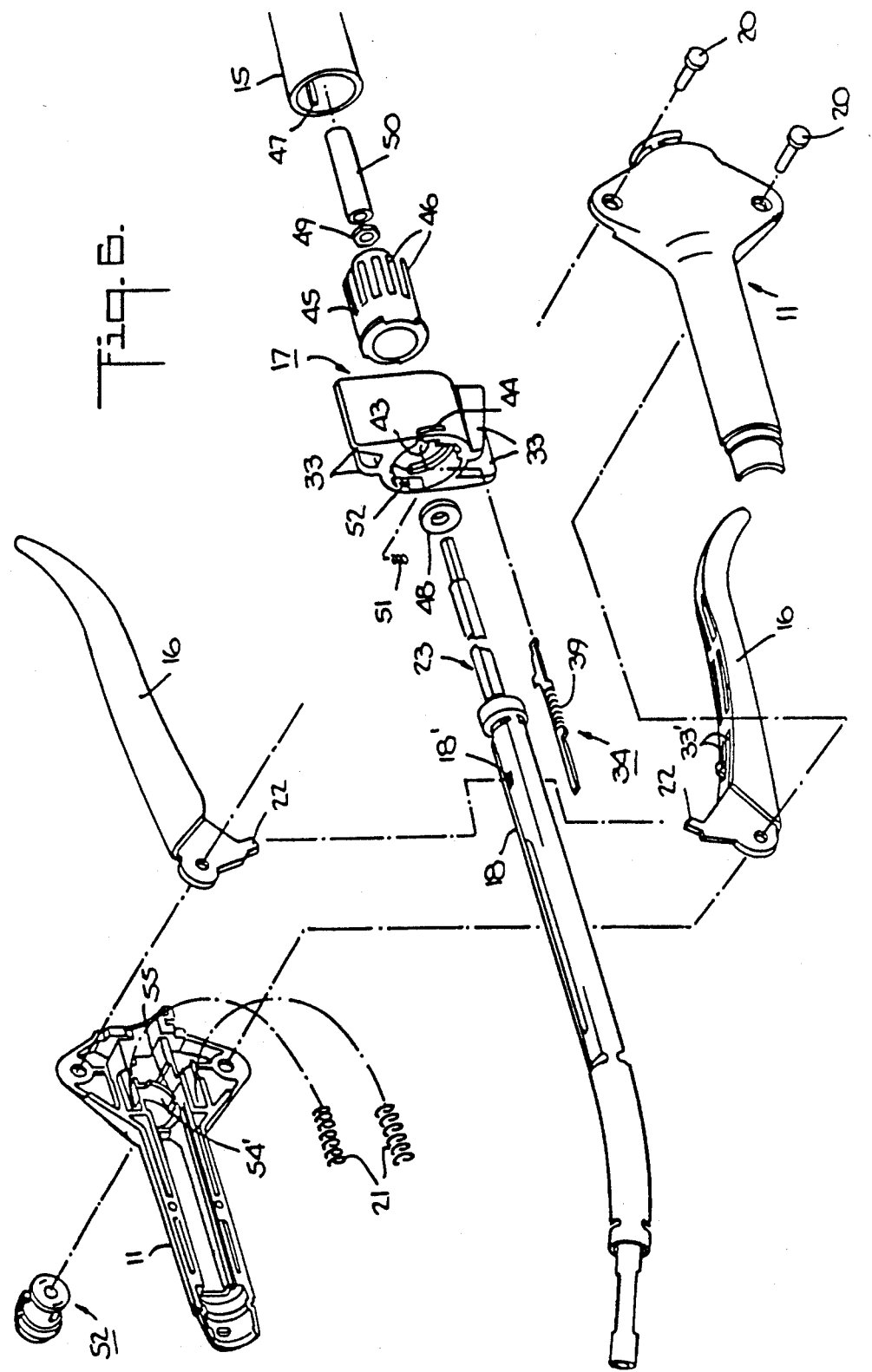

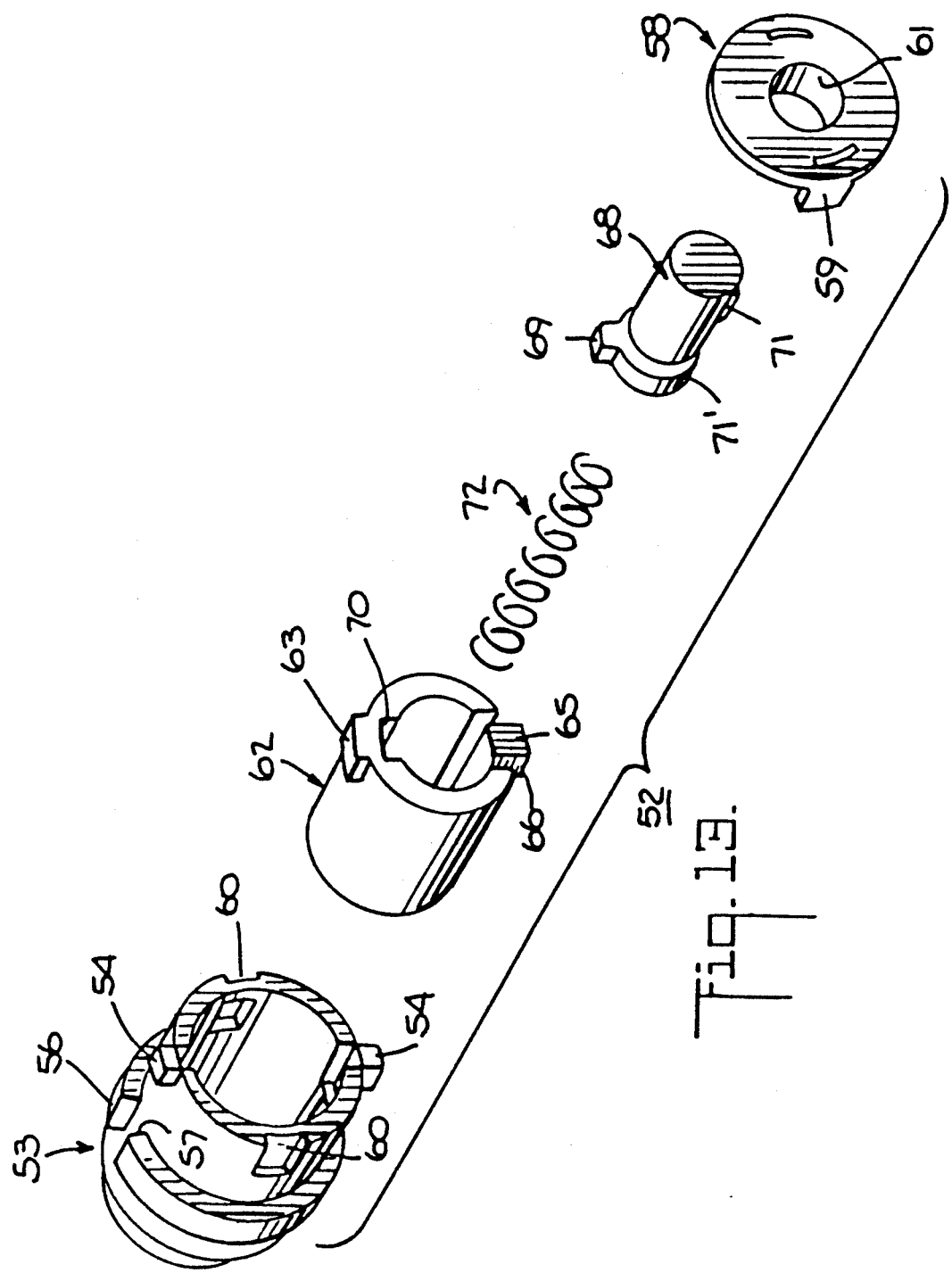

ANASTOMOSIS SURGICAL STAPLING INSTRUMENT

This is a division of U.S. application Ser. No. 214,289 filed Jul. 1, 1988, now U.S. Pat. No. 5,005,749.

This invention relates to an anastomosis surgical stapling instrument. More particularly, this invention relates to an arrangement for an anastomosis surgical stapling instrument.

As is known, various types of surgical stapler instruments have been known for the application of staples to tissue. For example, it has been known to use various types of staplers in gastric and esophageal surgery in both classic or modified gastric restructions performed end-to-end, end-to-side or side-to-side. In many cases, instruments, such as described in U.S. Pat. No. 4,603,693, have been used where an anvil assembly mounted on the end of a center rod can be manipulated relative to a staple assembly on the end of a tubular housing of the instrument. In instruments of this nature, the center rod is connected with a mechanism, for example, which employs a wing nut at the proximal end of the instrument, so that the rod can be moved back and forth independently of the staple assembly so as to adjust the anvil assembly relative to the staple assembly. Likewise, a pusher tube has been mounted within the instrument for movement via a handle mechanism so as to cause a firing of the staples from the staple assembly towards the anvil assembly.

In some cases, such as described in U.S. Pat. No. 4,351,466, these stapling instruments have been provided with a pair of handles in order to actuate the pusher tube to cause a firing of the staples. In such cases, each handle has been pivotally mounted so as to be moved toward the other handle during manual squeezing by a surgeon. Each handle also includes a lever arm within the instrument which engages against the pusher tube so as to move the tube in a proximal direction. However, it has been found, in some cases, that a jamming of the instrument occurs when the levers are closed down and the surgeon attempts to unclamp the tissue which has been stapled by backing off the wing nut. This jamming is caused by the lever arms engaging the center rod in a clamping grip so that the center rod cannot be moved forwardly, that is in the distal direction, so as to move the anvil assembly away from the tissue.

Stapling instruments of this type have also been provided with safety locks in order to prevent the squeezing together of the handles prematurely. That is, the safety locks have been provided in order to prevent the handles from moving towards each other before a surgeon has manipulated the anvil assembly into position for the firing of the staples. For example, U.S. Pat. No. 4,351,466 describes the use of a wire safety stop in order to fix the handles against movement. However, such a wire stop, upon removal, requires monitoring to ensure that the wire stop does not invade the patient or otherwise interfere with the surgical procedure. Further, care must be taken that the wire stop does not become inadvertently removed from the handles prior to the time at which removal is required.

Still further, another concern which arises with the use of these stapling instruments is that there is a need to know when the stapling instrument has been fired. For example, if the staples of an instrument have been prematurely fired, a surgeon may not realize that this has occurred from the physical appearance of the instrument. That is, if during manipulation, the handles have been inadvertently squeezed an amount sufficient to fire the staples, a surgeon may not realize that the staples have fired. In such cases, the surgeon may attempt to further manipulate the instrument in a patient prior to making an attempt to fire the staples. This, however, may cause damage to the tissue of the patient.

Accordingly, it is an object of the invention to eliminate clamping of the center rod of an anastomosis stapling It is another object of the invention to facilitate the release of an anvil assembly of an anastomosis stapling instrument after a stapling procedure has been performed.

It is another object of the invention to positively prevent the inadvertent firing of an anastomosis stapling instrument.

It is another object of the invention to provide a self-contained structure for preventing the inadvertent firing of a stapling instrument.

It is another object of the invention to provide a self-contained indicator to indicate the firing of an anastomosis stapling instrument.

It is another object of the invention to provide a positive indication of the firing of a stapling instrument.

Briefly, the invention is directed to an anastomosis surgical stapling instrument which is comprised of a yoke, a pusher tube slidably mounted within the yoke for actuation of a staple assembly at a distal end of the tube, a pair of handles pivotally mounted on the yoke for moving the pusher tube and a center rod reciprocably mounted coaxially within the pusher tube for relative movement thereto in order to manipulate an anvil assembly at a distal end relative to the staple assembly.

The pusher tube is provided with a pair of diametrically disposed openings near a proximal end while each handle has an arm extending through a respective opening in order to abut and move the pusher tube in a distal direction in response to pivoting of the handles towards each other.

In accordance with the invention, the center rod has a central portion within the pusher tube and a recessed portion extending proximally of the central portion to receive the arms of the handles therein in spaced relation during squeezing of the handles together. To this end, the recessed portion has a pair of flat parallel surfaces disposed in opposition and in spaced relation to the arms of the handles. In addition, the recessed portion has a curved surface between the flat surfaces which includes a thread segment thereon. In this respect, the recessed portion can be formed by milling a threaded section of the threaded rod on three sides to provide flat surfaces down to the inner diameter of the thread. Thus, the thread segment on the curved surface has a radius corresponding to the outer diameter of the thread. The strength of the center rod then remains the same as a threaded rod with respect to the forces required to move an anvil assembly secured to the center rod.

The instrument also includes a safety lock Which is rotatably mounted on the yoke between the handles. This lock the handles toward each other and a release position to permit movement of the handles toward each other. In accordance with the invention, a self-contained slide assembly is provided within the instrument to prevent rotation of the safety lock from the locking position. In this respect, the slide assembly is responsive to movement of the center rod in order to move from a blocking position preventing rotation of the safety lock from the locking position to the release position and a release position to permit rotation of the safety lock. This release position of the slide assembly corresponds to the stapling position of the stapling assembly. Thus, the center rod can be manipulated so as to move the anvil assembly into appropriate position for stapling while the safety lock is positively prevented from moving out of the locking position thereof. Once the anvil assembly has been moved into the appropriate position, the slide assembly which is responsive to the movement of the center rod is in a release position permitting the safety lock to be rotated into the release position thereof in order to permit movement of the handles toward each other for firing of the staple assembly.

The slide assembly may be constructed of a slide plate which is slidably mounted within the yoke of the instrument. In this case, the slide plate has a depending leg which projects into the annular grove of the center rod and which is biased by a spring against the distal portion of the center rod. A suitable slot is also provided in the pusher tube to accommodate passage of the leg of the slide plate into the groove of the center rod.

In order to provide for blocking of the rotation of the safety lock by the slide assembly, the safety lock is provided with a radially disposed stop while the slide assembly has a radially outwardly directed arm at a proximal end for butting against the stop in the blocking position of the slide assembly. Thus, when the arm is moved proximally out of alignment with the stop, the safety lock is free to rotate. In order to provide a visual indication of the unlocking of the safety lock, an arcuate circumferential slot is provided in the safety lock adjacent the stop in order to visually expose the arm of the slide assembly to view. Thus, the arm may act as a "flag" to indicate that the safety lock is free to rotate.

The instrument is may also be provided with an indicator device which is mounted in the yoke and which is responsive to movement of the pusher tube in order to indicate the movement of the pusher tube to a fired position. The indicator device may be in the form of a self-contained device which can be mounted in a side of the yoke so as to respond to the staple assembly has been fired.

The indicator device is constructed of a housing which defines an open-ended cavity and a bearing cap which is mounted on the housing at the open end and which is provided with a center opening. In addition, an indicator is mounted in the housing for movement between a fixed first position and a second position. To this end, a plunger is moveably mounted within the indicator for movement between a recessed position relative to the housing and an extended position projecting from the opening of the bearing cap. This plunger also has means for holding the indicator in the first fixed position when the plunger is in the recessed position. A spring is also provided for biasing the plunger from the recessed position within the housing toward the extended position.

The indicator device is positioned so that the spring biased plunger abuts against the pusher tube. Once the pusher tube has been moved by the handles of the instrument to a fired position, the plunger springs into a slot in the pusher tube. As the plunger moves through the bearing cap, the indicator is released from the fixed position so that the spring also biases the indicator radially outwardly of the instrument. In this respect, the indicator carries a button which can be moved into an aperture of the housing for viewing. The button, for example being provided with a suitable color, may serve as a signal that the instrument has fired.

These and other objects and advantages of the invention will become more apparent from the following detailed description taken in conjunction with the accompanying drawings wherein:

FIG. 1 illustrates a perspective view of an anastomosis surgical stapling instrument constructed in accordance with the invention;

FIG. 2 illustrates a cross-sectional view of a part of the instrument of FIG. 1:

FIG. 3 illustrates a perspective view of a center rod constructed in accordance with the invention; and FIG. 4 illustrates a view taken on line 4—4 of FIG.

FIG. 6 illustrates an exploded view of the instrument in FIG. 1;

FIG. 13 illustrates an exploded view of the indicator device in accordance with the invention.

Figure 5:
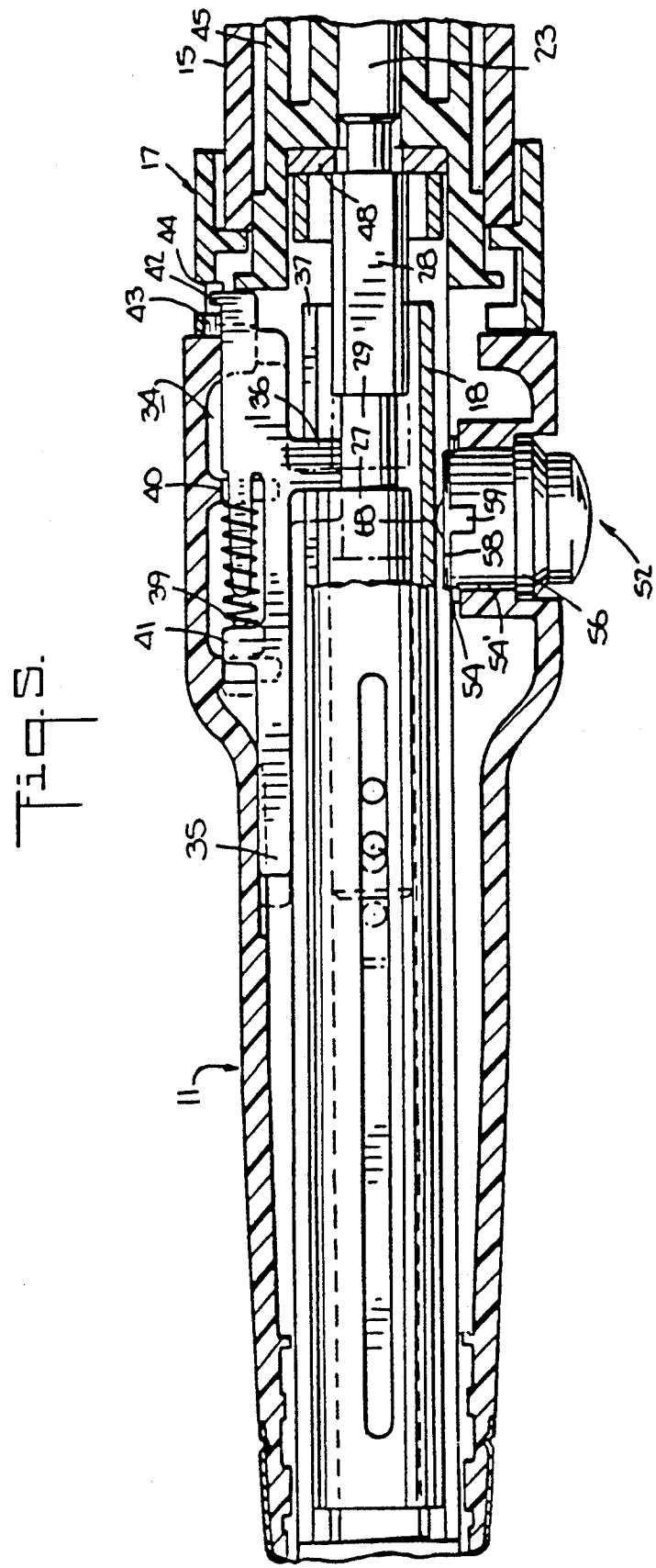
FIG. 5 illustrates a cross-sectional view of a part of the instrument having a slide assembly and indicator device in accordance with the invention.

Referring to FIG. 1, the anastomosis surgical stapling instrument 10 is of generally conventional structure. For example, the instrument 10 includes a yoke 11, a pusher tube assembly 12 which extends from the yoke 11 to carry a staple assembly 13 at the distal end, an anvil assembly 14 at the distal end of the instrument and an actuating mechanism which extends from the anvil assembly 14 through the pusher tube assembly 12 to a wing nut 15 at the proximal end of the instrument for moving the anvil assembly 14 relative to the pusher tube assembly 13. In addition, a pair of handles 16 is pivotally mounted on the yoke 11 to provide for movement of the staple assembly 13 against the anvil assembly 14. These handles 16 are mounted so as to be manually grasped by a surgeon and moved towards each other as indicated by the arrows assembly 13 towards the anvil assembly 14. A safety lock 17 is also mounted on the proximal end of the yoke 11 to prevent inadvertent movement of the handles 16 towards each other.

Referring to FIG. 2, the pusher tube assembly 12 includes a pusher tube 18 which is slidably mounted within the yoke 11 to engage the staple assembly 13 at the distal end in known manner. The tube 18 has a pair of diametrically disposed openings 18' near a proximal end as well as a pair of diametrically disposed elongated slots 19 extending within the yoke 11.

Each handle 16 is pivotally mounted via a pin 20 in the yoke 11 and is biased by a spring 21 to move away from the safety lock 17. In addition, each handle 16 has a lever arm 22 which extends inwardly of the yoke 11 and passes through an opening 18' in the pusher tube 18. Upon pivoting of the handles 16 towards each other, the lever arms 22 abut and push the pusher tube 18 in a distal direction.

A center rod 23 of a metal suitable to transfer a high load is reciprocably mounted coaxially within the pusher tube 18 for relative movement thereto. As indicated in FIGS. 2 and 3, the forward end of the rod 23 is provided with a slot 24 which receives a band assembly 25 and which is secured thereto by a pair of pins 26. The band assembly 25, in turn is connected to the anvil assembly 13 (see FIG. 1) in any suitable manner as is known. As indicated in FIG. 2, one of the pins 26 is of elongated shape so as to slide within the slots 19 of the outer tube 17. The slots 19 thus limit the excursion of the center rod 23 and thus the anvil assembly 14 relative to the staple assembly 13.

For example, the center rod 23 may be manipulated by the wing nut 15 of actuating mechanism so as to move forwardly and rearwardly so as to adjust the anvil assembly 14 to the thickness of tissue located between the anvil assembly 14 and staple assembly 13. Once the anvil assembly 14 has been located, the handles 16 can be squeezed together to move the center tube 18 in the distal direction so as to fire the staples (not shown) from the staple assembly 13.

Referring to FIGS. 3 and 4, the center rod 23 is provided with a distal portion 27, a recessed portion 28 and an annular groove 29 between the portions 27, 28. The recessed portion 28 which is originally formed as a threaded portion having an outer diameter equal to the outer diameter of the distal portion 27 is milled or otherwise worked so as to have three flat surfaces formed thereon while leaving a curved surface 31 with a thread segment 32 thereon. In this respect, the flat surfaces 30 are tangent to the inner diameter of the original threads so that the strength of the center rod is not weakened. On the other hand, a pair of the flat surfaces 30 are disposed in opposition to the openings 18' in the pusher tube 18 so as to provide a clearance C with an arm 22 of the handle 16 when the handle 16 has been moved into a forwardmost position, for example as indicated in FIG. 2.

Referring to FIG. 2, after the center rod 23 has been adjusted into a position to fix the anvil assembly 14 relative to the staple assembly 13 (FIG. 1), the handles 16 can be squeezed together. At this time, such lever arm 22 abuts and pushes the tube 18 forwardly, for example to a point at which the arms 22 of the handles 16 move into the annular groove 29 of the center rod 23 towards the distal portion 27. However, during this time, the arms 22 clear the flat surfaces 30 of the recessed portion 28. Since the arms 22 are always spaced from the flat surfaces 30 of the recessed portion 29 as well as from the base of the groove 29, the center rod 23 can be moved forwardly after firing of the staples to separate the anvil assembly 14 away from the staple assembly 13 and the stapled tissue therebetween with the handles 16 fully or partially in a closed together position. Further, a forward movement of the center rod 23 relative to the arms 22 can be accommodated prior to firing which might otherwise align the arms 22 with the flat surfaces 30.

Referring to FIG. 5, the safety lock 17 is mounted on the proximal end of the yoke 11 in order to be rotatable between a locking position to prevent movement of the handles 16 toward each other and a release position to permit movement of the handles 16 toward each other. In this respect, the safety lock 17 has a pair of flanges 33 at diametric points for fitting into grooves 33' (FIG. 6) of the handles 16 to prevent movement of the handles toward each other.

Referring to FIG. 5, a slide assembly 34 is provided to prevent rotation of the safety lock 17 from the locking position to the release position. This slide assembly 34 is self contained within the yoke 11 and is responsive to the movement of the center rod 23. In this respect, the slide assembly is coordinated with the position of the center rod 23 and, thus, the anvil assembly 14 (FIG. 1) so that the safety lock 17 cannot be rotated out of the locking position until the anvil assembly 14 has been properly position for a stapling operation.

Figure 7:
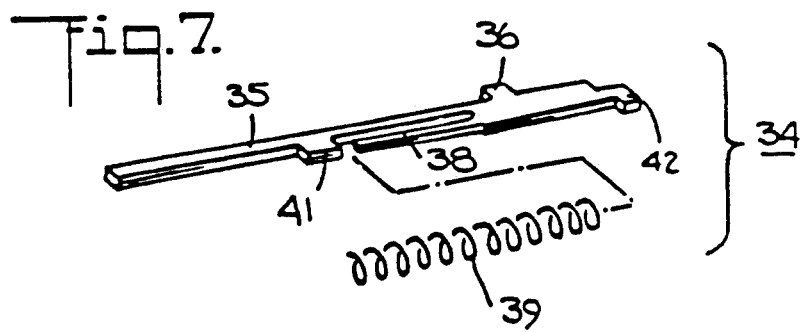
FIG. 7 illustrates an exploded view of a slide assembly in accordance with the invention.

Referring to FIGS. 5 and 7, the slide assembly 34 is formed by a flat slide plate 35 and a spring 39. As shown in FIG. 5, the plate 35 is slidably mounted within the yoke 11 and has a depending leg 36 which projects through a slot 37 in the pusher tube 18 into the annular groove 29 of the center rod 23. The plate 35 also has a longitudinally extending finger 38 about which a coil spring 39 is mounted. The spring 39 abuts against a rib 40 within the yoke 11 and, at the distal end, against a second leg 41 of the plate 35 so as to bias the plate 35 distally. In this way, the inwardly directly leg 36 is biased against the distal portion 27 of the center rod 23. Thus, the plate 35 follows the movement of the center rod 23 in both the distal direction and the proximal direction.

Figure 8:
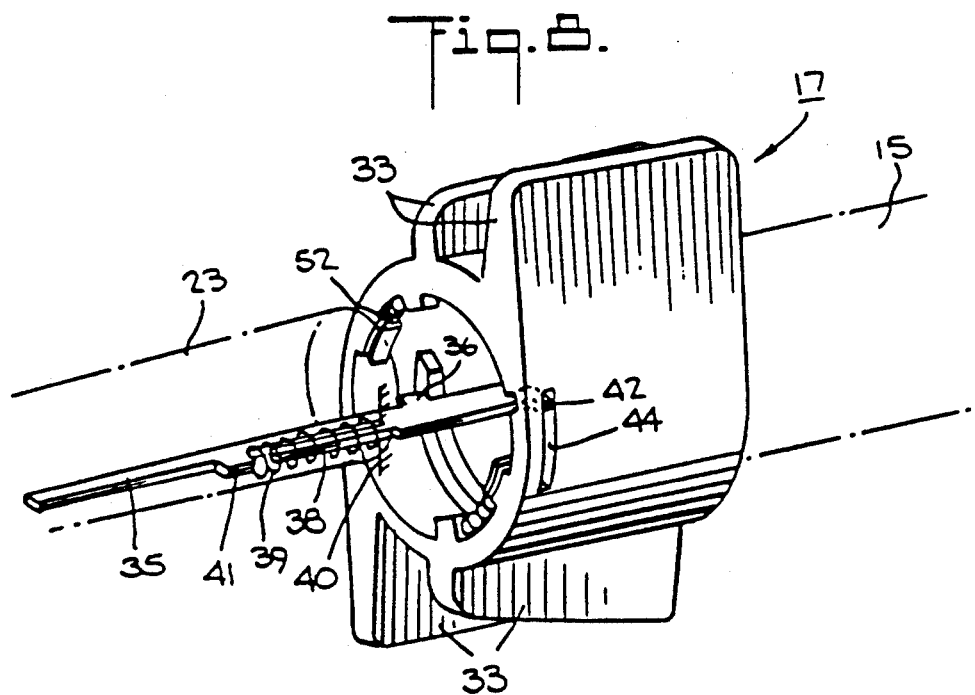
FIG. 8 illustrates a perspective view of the slide assembly in cooperation with the safety lock of the instrument.
Figure 9:
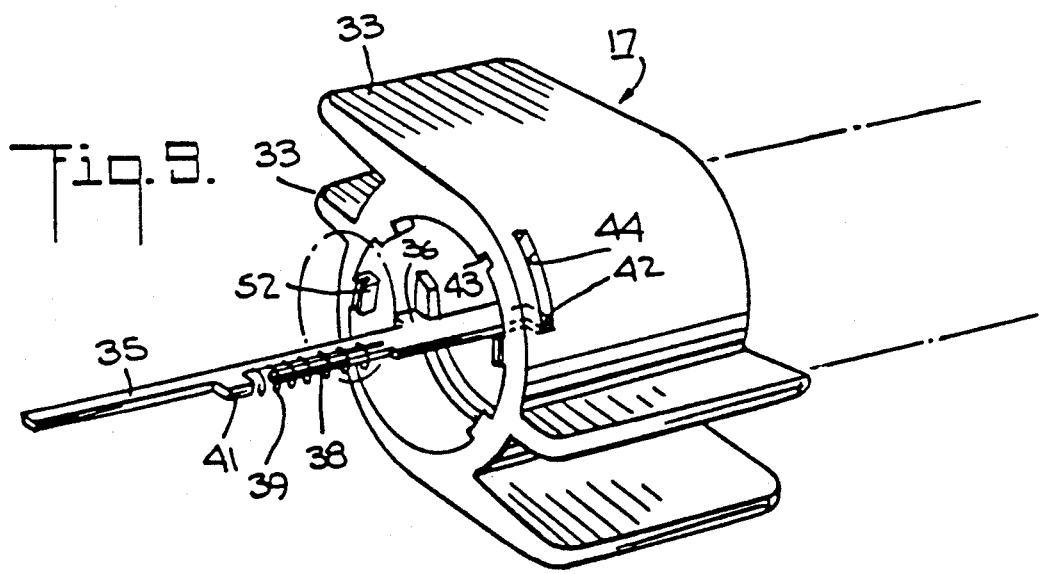
FIG. 9 illustrates a perspective view of the slide assembly and safety lock with the safety lock in a released position.

The plate 35 also has a radially outwardly directed arm 42 at the proximal end which is accommodated in a groove 43 of the safety lock 17 (See FIG. 8). The groove 43 serves as a stop to abut the arm 42 such that the safety lock 17 cannot be rotated while the arm 42 is within the groove 43. In addition, the safety lock 17 has an arcuate circumferential slot 44 adjacent the groove 43 to receive the arm 42. When the arm 42 is received within the slot 44, the safety lock 17 is freed to move from the locked position of FIG. 8 to the release position of FIG. 9.

Referring to FIGS. 5 and 6, a wing nut insert 45 is rotatably mounted within the yoke 11 and safety lock 17 in known manner. This insert 45 is provided with a plurality of splines 46 which defines grooves into which an internal rib 47 on the wing nut 15 is fitted in order to transfer rotation of the wing nut 15 to the threaded portion of the center rod 23.

As indicated in FIGS. 5 and 6, a washer 48 is disposed within the insert 45 in abutment with an internal wall. In addition, a stop nut 49 is threaded onto the center of the rod 23 to indicate the position of the center rod 23 by means of an opening in the wing nut 15 as is known.

Referring to FIG. 6, the safety lock 17 is provided internally with a compression spring 51 which serves to bias the safety lock 17 into the locking position. This spring 51 abuts against a shoulder 52 within the safety lock 17 and a suitable shoulder within the yoke 11.

Referring to FIG. 5, the instrument 10 also includes an indicator device 52 which is mounted in the yoke 11 and which is responsive to movement of the pusher tube 18 in order to indicate movement of the pusher tube 18 to a fired position thereof.

Figure 10:
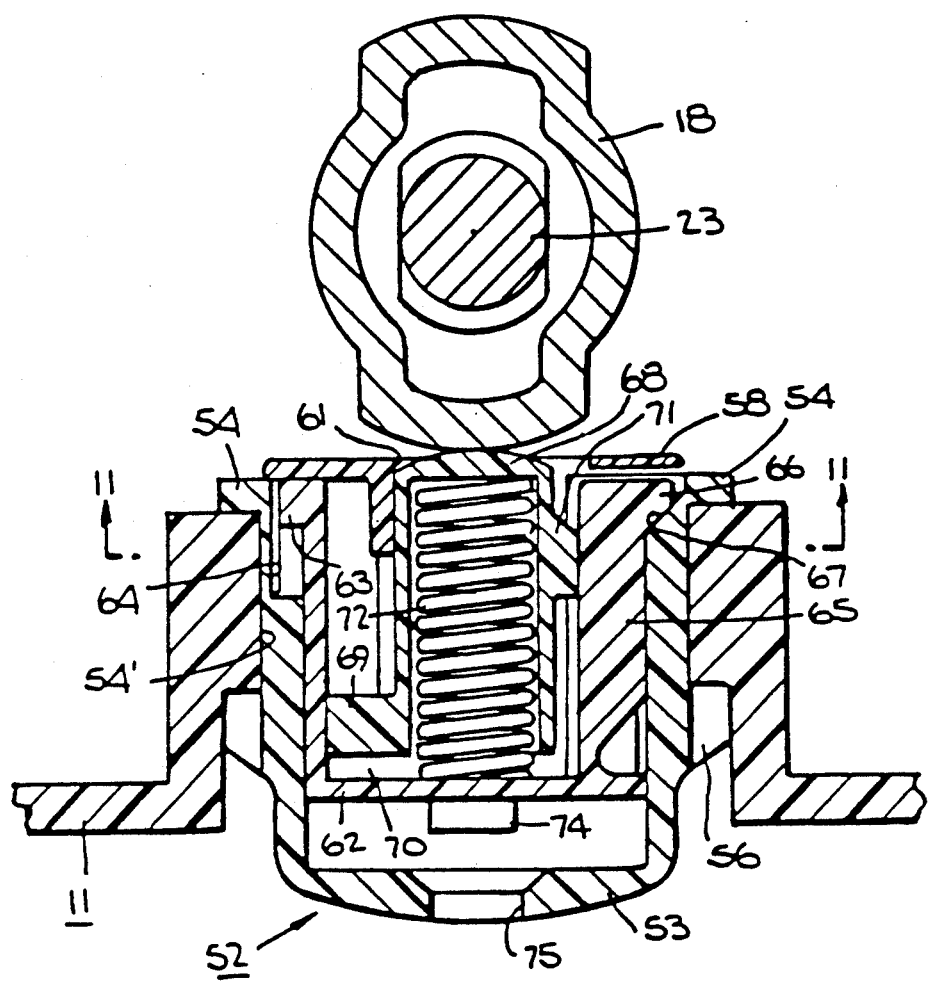
FIG. 10 illustrates a cross-sectional view of an indicator device disposed within the instrument.
Figure 11:
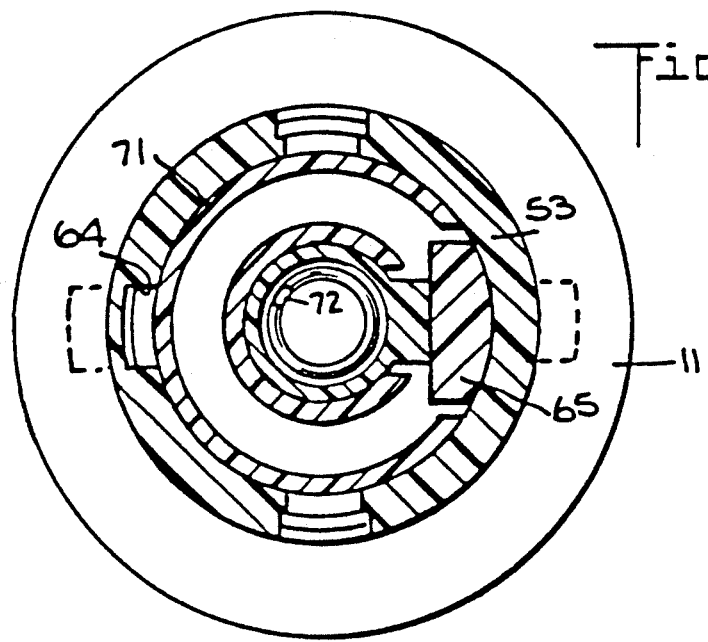
FIG. 11 illustrates a view taken on line 11—11 of FIG. 10.

Referring to FIG. 10, the indicator device 52 includes a housing 53 which is slidably mounted within a bore 54' in the yoke 11. As indicated in FIG. 13, the housing 53 is of cup-shape to provide an open ended cavity. In addition, the housing 53 has a pair of diametrically opposed tabs 54 which slide through grooves 55 (See FIG. 6) in the yoke 11 in order to permit mounting of the housing 53 therein. In this respect, after axially movement through the groove 55, the housing 53 is rotated, for example 90°. In addition, the housing 53 has an external circumferential rib 56 which is provided with interruptions 57 aligned with the tabs 54. The rib 56 serves to abut against a shoulder of the yoke 11 so that the housing 53 can be securely held in place.

The indicator device 52 also has a bearing cap 58 which is snap-fitted onto the open end of the housing 53. To this end, as indicated in FIG. 13, the bearing cap 58 has a pair of tangs 59 which are snap-fitted into apertures 60 in the housing 53. The bearing cap 58 is also provided with a central opening 61.

Figure 12:
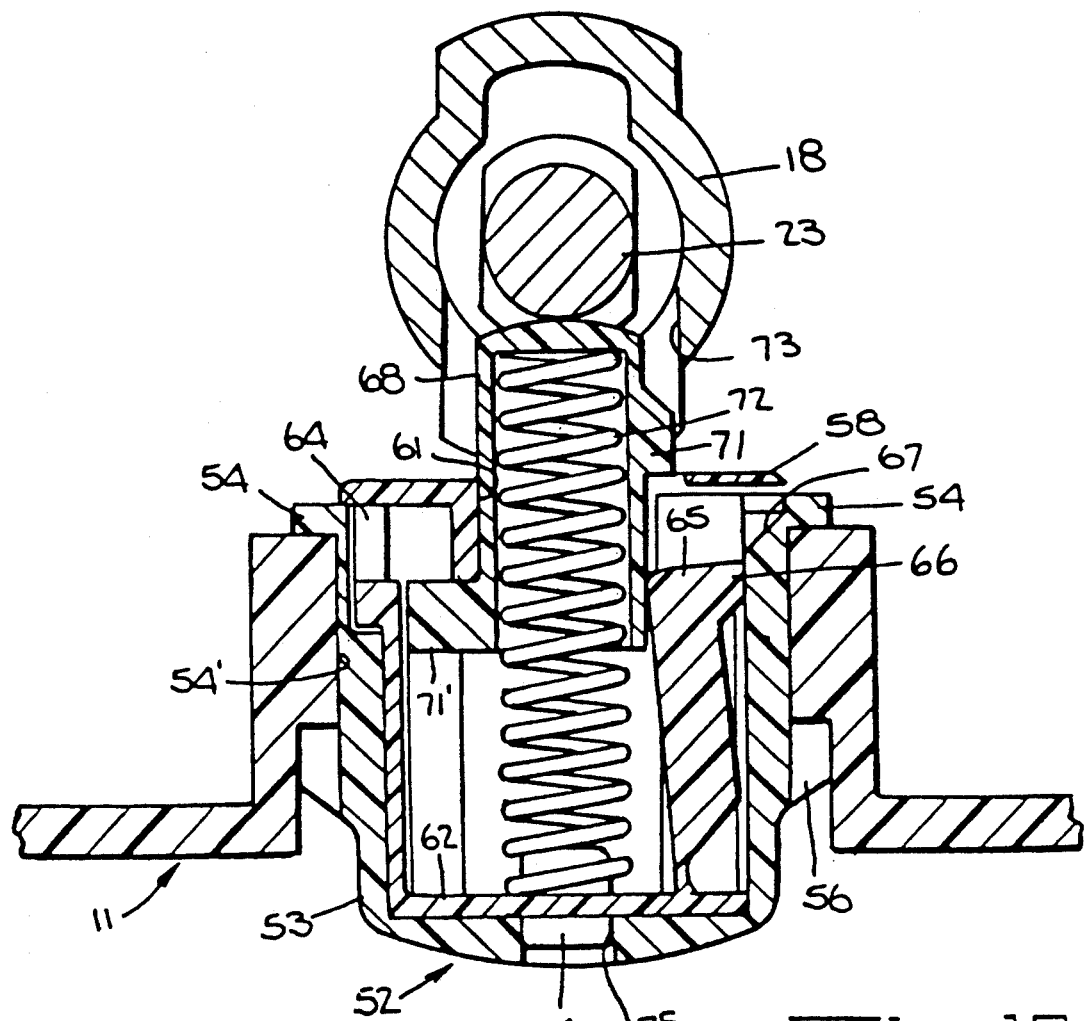
FIG. 12 illustrates a cross-sectional view of the indicator device in a fired position.

The indicator device 52 also has an indicator 62 which is mounted within housing 53 for movement from a fixed first position as shown in FIG. 10 to a second extended position as shown in FIG. 12. As indicated in FIG. 13, the indicator 62 is of generally cylindrical shape and carries a guide block 63 near an open end which is slidably received within a guide slot 64 of the housing 53 for alignment purposes Diametrically opposite the guide block 63 is a longitudinally extending pivotal leg 65 which has a radially outwardly directed cam surface 66 for matingly engaging a cam surface 67 on the housing 53 when in the fixed first position of FIG. 10. As indicated in FIG. 10, the leg 65 has a weakened portion to permit radially pivoting As indicated in FIG. 10, the indicator 62 is retained within the housing 53 by the bearing cap 58.

A plunger 68 is movably mounted within the indicator 62 for movement between a recessed position as shown in FIG. 10 and an extended position as shown in FIG. 12 projecting through the opening 61 of the bearing cap 58. This plunger 68 includes a guide block 69 which is slidably received within a guide slot 70 of the indicator 62. In addition, the plunger 68 has a means in the form of a cam 71 for holding the indicator 62 in the fixed position of FIG. 10. As indicated, the cam 71 engages the leg 65 to prevent radially inward movement of the leg 65 The plunger 68 also has a partial collar 71' for sliding on the interior of the indicator 62.

A coil spring 72 is disposed within the plunger 68 for biasing the plunger 68 from the recessed position of the FIG. 10 into the extended the position of FIG. 12. In this regard, when the plunger 68 is in the recessed position, the plunger 68 abuts the pusher tube 18 (See also FIG. 5). When the pusher tube 18 is moved distally, a slot 73 in the pusher tube 18 which is longitudinally aligned with the plunger 68 comes into radial alignment with the plunger 68. At this time, the spring 72 forces the plunger 68 radially inwardly of the yoke 11 into the recessed position shown in FIG. 12. At the same time, as the cam 71 of the plunger passes by the leg 65 of the indicator 62 and through the aperture 61 and the bearing cap 58. The leg 65 then pivots inwardly away from the cam surface 67. Thus, the spring 72 will also bias the indicator 62 into the position shown in FIG. 12 against the housing 53. In this respect, the indicator 62 carries a button 74 which projects into a central aperture 75 of the housing 53. This button 74 may be colored so as to provide a visual read-out that the instrument has been fired.

In use, the instrument 10 is manipulated in any conventional manner by a surgeon to the site at which stapling is to be performed. At that time, the wing nut 15 (See FIG. 1) is rotated so as to move the anvil assembly 14 into the appropriate position for stapling of the tissue of the patient. During this time, the safety lock 17 remains in the locked position of FIG. 1 and is prevented from rotating into the release position. Once the anvil assembly 14 has been located, the safety lock 17 is released. In this respect, as indicated in FIG. 8, the arm 42 of the slide plate 35 of the slide assembly 34 has moved through the groove 43 of the safety lock 17 into the arcuate slot 44. Thus, the safety lock 17 can be rotated into the release position of FIG. 9 so that the handles 16 of the instrument can be squeezed together.

During squeezing of the handles 16 together, the pusher tube 18 (See FIG. 2) is moved in the distal direction to fire the staples. At the same time, the slot 73 of the pusher tube 18 (See FIG. 12) moves into alignment with the plunger 68 of the indicator mean 52 so that the plunger 63 releases and the button 74 of the indicator 62 pops into the opening 75 of the housing 53 to indicate that firing of the staples has taken place.

Thereafter, the center rod 23 can again be moved via the wing nut 15 in a distal direction to separate the anvil assembly 14 for the staple assembly 13 for manipulation of the instrument 10 out of the patient At this time, the recessed portion 28 of the center rod 23 passes by the arms 22 of the handles 16 with a clearance so as to avoid jamming of the instruments.

The invention thus provides an anastomosis surgical stapling instrument in which jamming of the handles of the instrument can be eliminated after firing of the staples.

The invention also provides an anastomosis surgical stapling instrument in which the safety lock of the instrument can be positively secured in a locking position by a self-contained slide assembly. Thus, there are no loose parts which can be misplaced during a surgical procedure. Still further, the instrument may be fired only when the anvil assembly has been properly position as the safety lock cannot be otherwise released.

The invention also provides a positive indication of the firing of the staples from the staple assembly.

What is claimed is:

1. An indicator device for an anastomosis surgical stapling instrument having a slidable pusher for engaging a staple assembly comprising
a housing defining an open-ended cavity;
an indicator mounted in said housing for movement from a first position to a second position;
a plunger movably mounted within said indicator for movement between a recessed position and an extended position to indicate firing of the staples, said plunger having means for holding said indicator in said first position with said plunger in said recessed position, said plunger being movable in response to sliding movement of said pusher; and
a spring biasing said plunger from said recessed position towards said extended position.

2. An indicator device as set forth in claim 1 wherein said indicator has a longitudinally extending pivotal leg having a radially outwardly directed cam surface engaging a mating cam surface on said housing in said first position whereby in said recessed position of said plunger, said means on said plunger engages said leg and in said extended position of said plunger said means disengages from said leg to permit radial inward movement thereof and movement of said indicator into said second position.

3. An indicator device as set forth in claim 1, wherein said housing is cup-shaped and has a centrally disposed aperture and said indicator has a projecting button for disposition in said opening in said second position thereof.

4. An indicator device as set forth in claim 1 wherein said indicator is of cylindrical shape and is slidably guided in said housing and wherein said plunger is slidably guided within said indicator.

5. An indicator device as set forth in claim 4 wherein said indicator has a longitudinally extending pivotal leg having a radially outwardly directed cam surface engaging a mating cam surface on said housing in said first position whereby in said recessed position of said plunger, said means on said plunger engages said leg and in said extended position of said plunger said means disengages from said leg to permit radial inward movement thereof and movement of said indicator into said second position.

6. In a circular anastomosis surgical instrument having a fastener assembly containing an annular array of fasteners and a pusher tube slidably mounted in an instrument housing for engagement with said fastener assembly, the improvement comprising means for indicting the firing of the fasteners, said indicting means mounted adjacent said pusher tube, said indicating means radially movable with respect to said pusher tube between a first position and a second position to indicate firing of the fasteners.

7. A surgical instrument as recited in claim 6 wherein said indicating means is biased towards said second position.

8. A surgical instrument as recited in claim 7 wherein said pusher tube comprises a recess, said recess receiving a portion of said indicating means when said pusher tube is moved distally a sufficient distance to fire the fasteners to thereby allow said indicating means to move outwardly towards said second position.

9. A surgical instrument as recited in claim 8 further comprising means for releasing said indicating means from said first position to allow movement to said second position.

* * * * *